United States Patent
McNichols et al.

(10) Patent No.: US 6,671,535 B1
(45) Date of Patent: *Dec. 30, 2003

(54) METHOD AND SYSTEM FOR CONTROLLING HEAT DELIVERY TO A TARGET

(75) Inventors: Roger J. McNichols, Bryan, TX (US); Ashok Gowda, College Station, TX (US)

(73) Assignee: Biotex, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/324,973

(22) Filed: Dec. 20, 2002

Related U.S. Application Data

(63) Continuation of application No. 09/710,694, filed on Nov. 8, 2000, now Pat. No. 6,542,767.
(60) Provisional application No. 60/164,416, filed on Nov. 9, 1999.

(51) Int. Cl.$^7$ ............................... A61B 5/00; A61N 7/00
(52) U.S. Cl. ..................... 600/407; 600/410; 600/459; 600/442; 607/96; 607/100
(58) Field of Search .......................... 607/96, 100, 102; 600/407, 410, 411, 412, 437, 438, 442, 549

(56) References Cited

U.S. PATENT DOCUMENTS 4,515,165 A * 5/1985 Carroll ........................ 600/475
4,633,875 A * 1/1987 Turner ......................... 607/98
5,501,655 A * 3/1996 Rolt et al. ..................... 601/3
6,542,767 B1 * 4/2003 McNichols et al. ......... 600/407

FOREIGN PATENT DOCUMENTS

| JP | 2000-217835 A | * | 8/2000 | ........... A61B/17/32 |
| JP | 2001-46523 A | * | 2/2001 | ........... A61N/1/40 |
| WO | WO 02/00298 A1 | * | 2/2002 | ........... A61N/7/00 |

* cited by examiner

*Primary Examiner*—Hieu T. Vo
(74) *Attorney, Agent, or Firm*—Toler, Larson & Abel, LLP

(57) ABSTRACT

A method and system for using real time closed loop feedback to control the delivery of heat energy is disclosed herein. An energy delivery system may be used to deliver heat energy to a target to effect a change in the target. For example, medical professionals use laser energy to irreversibly damage cells found in cancerous tumors without damaging the surrounding healthy cells. The energy delivery system includes a temperature detection system, a data processor, and a heat generating device. The temperature detection system obtains temperature data from a target and transmits the data to the data processor. The data processor may process the temperature data to provide real time feedback control to the heat generating system, as well as display the data as one or more images on a graphical user interface. The heat generating system receives control commands from the data processor and modulates its heat output accordingly.

82 Claims, 8 Drawing Sheets

METHOD AND SYSTEM FOR CONTROLLING HEAT DELIVERY TO A TARGET

PRIORITY APPLICATION

This application is a continuation of U.S. application Ser. No. 09/710,694, filed on Nov. 8, 2000, now U.S. Pat. No. 6,542,767 B1, issued on Apr. 1, 2003 entitled METHOD AND SYSTEM FOR CONTROLLING HEAT DELIVERY TO A TARGET, which claims benefit of U.S. Provisional Patent Application Serial No. 60/164,416 filed Nov. 9, 1999, entitled "METHOD AND SYSTEM FOR CONTROLLING HEAT DELIVERY TO A TARGET" of common assignee herewith.

FIELD OF THE INVENTION

The present invention relates generally to controlling heat delivered to a target, and more particularly to controlling heat delivered to a target based upon temperature sensitive information from a device that interrogates a target with radiation as part of acquiring input data used for controlling heat delivery.

BACKGROUND OF THE INVENTION

It is recognized in the medical industry that undesirable lesions can be treated through their removal. It is known to have a practitioner, such as a doctor, physically remove such lesions through surgery. It is also known to have a practitioner destroy lesions by controlling an application of heat local to the lesion. Known processes whereby a practitioner destroys the lesion by using heat require the practitioner to control the process based on visual data and temperature data. Based upon this information, the practitioner will modify the heat source to change an attribute of the heat, such as its location, direction, and intensity. The proper application of the heat delivery process is dependent upon the ability of the practitioner to interpret available visual and temperature data, and to implement an appropriate treatment in response. As a result, the ability to control processes in a predictable manner varies between practitioners, and even varies day-to-day for a given practitioner.

Therefore, a method and or system that allows for improved control in treating a target, such as a lesion, would be useful.

DETAILED DESCRIPTION OF THE DRAWINGS

In accordance with at least one embodiment of the present invention, data is received at a data processor from a temperature detection system, wherein the data corresponds to a material, such as a tissue portion, and includes temperature sensitive information. The data processor determines a first characteristic for a heat generating device based on the temperature information. Additionally, the data processor provides the heat generating device control data based on the first characteristic to control the heat generating device. One advantage of the present invention is that it is possible to provide a method for non-invasively determining the temperature distribution inside of an object, and in real time or near real time using the temperature distribution and/or damage distribution of the material to control an excessive heat output and/or to avoid an insufficient heat output, or to otherwise effect a desired result.

FIGS. 1–8 illustrate an energy delivery system in accordance with a specific embodiment of the present invention having one or more temperature detection systems, one or more data processors, and one or more heat generating systems, as well as a method for its use. As described in greater detail below, the energy delivery system uses a temperature detection system to either periodically or continuously measure the temperature and/or cell damage of a target receiving heat energy. In at least one embodiment, a user inputs desired parameters to define a control strategy for the heat generating system. The data processor uses the control strategy to govern the behavior of the heat generating system in real time, or near real time, using feedback from the temperature detection system. The data processor is also capable of displaying temperature, damage, and structure images to the user, as well as inputting user-defined parameters, with a graphical user interface (GUI).

Figure 1:
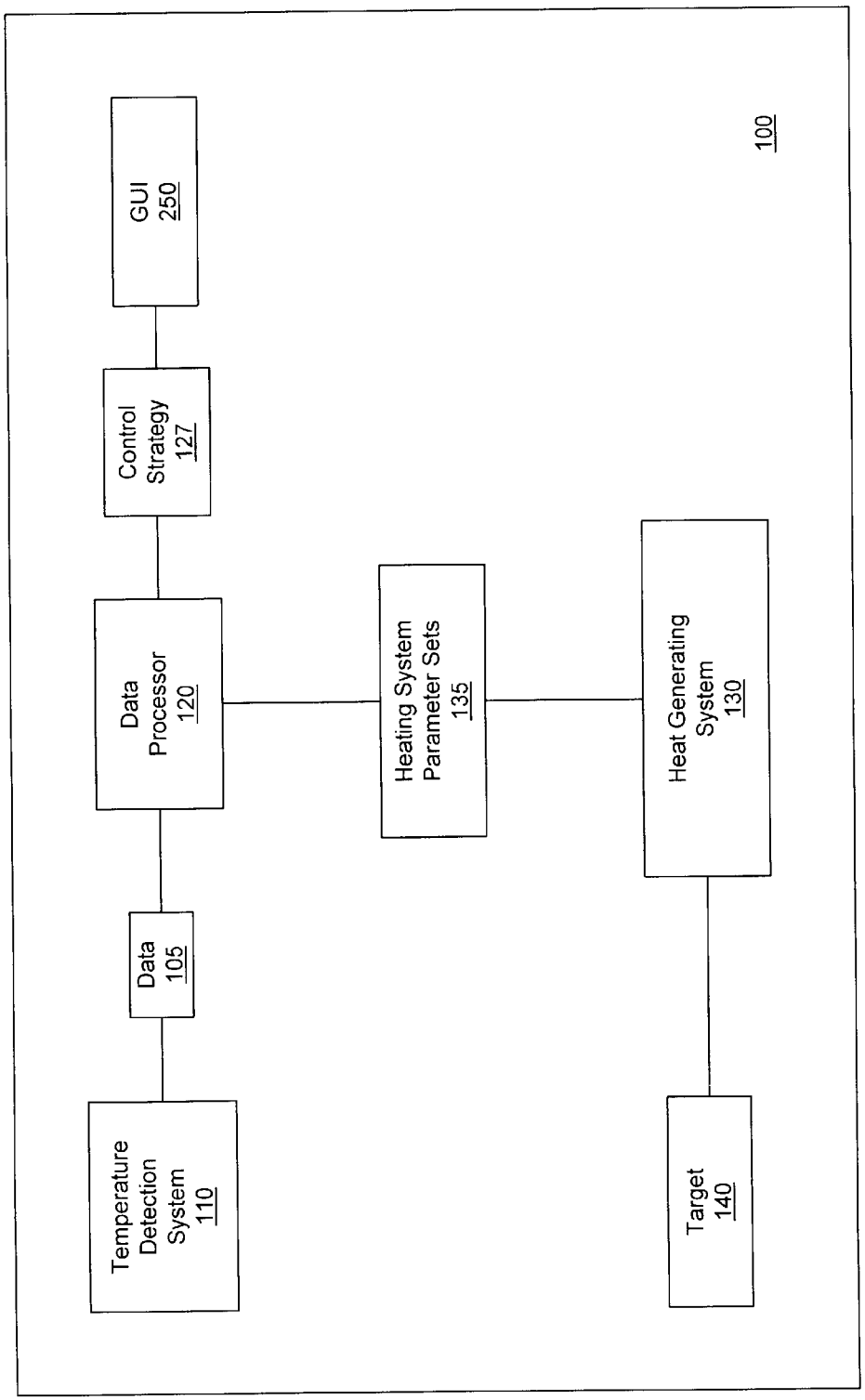
FIG. 1 is a diagram illustrating a real time feedback-controlled energy delivery system according to at least one embodiment of the present invention.

Referring now to FIG. 1, a feedback-controlled energy delivery system 100 is illustrated according to one embodiment of the present invention. Energy delivery system 100 includes temperature detection system 110, data processor 120, and heat generating system 130. Temperature detection system 110 includes a device that uses radiation to interrogate a target or other suitable system capable of acquiring temperature information of target 140. In one embodiment, target 140 includes a biological tissue to be destroyed by heating, or any other object having specific localized areas to be heated without damaging surrounding areas. Temperature detection system 110 may include a magnetic resonance device, an ultrasound device, an infrared device, a radio frequency device, x-ray device, infrared detection device, computerized topography (CT) device, and the like.

Data processor 120 can include any data processing system capable of receiving and processing data from temperature detection system 110 to control, on a real-time or near real-time basis, heat generating system 130. Data processor 120 may include a workstation, personal computer, supercomputer, dedicated hardware, and the like. Heat generating system 130 can include any device capable of generating heat, or energy that may be transformed to heat, and further capable of conveying this heat or energy to target 140 via one or more applicators. Heat generating system 130 may include a laser device, a microwave device, a resistive heater, and the like. It will be appreciated that data processor 120 may be either locally or remotely connected to temperature detection system 110 and heat generating system 130. It will also be appreciated that energy delivery system 100 may include more than one of each of temperature measuring system 110, data processor 120, and heat generating system 130 without departing from the spirit or the scope of the present invention.

In one embodiment of the present invention, temperature detection system 110 is capable of obtaining temperature sensitive data on a periodic or continuing basis. The temperature sensitive data can represent the absolute or relative temperature distribution of a point, area, plane, contour, or volume of a portion of target 140. For example, a magnetic resonance device can be used to capture data to be processed for determining the structure of selected portions of target 140, as well as the selected portions' relative temperature distribution at a given point in time. After temperature detection system 110 captures data 105 from target 140 for one cycle, data 105 may be either stored in a database in temperature detection system 110 and transmitted at a later time to data processor 120, or the captured data (data 105) may be immediately sent to data processor 120. It will be appreciated that temperature detection system 110 may pre-process data 105 before it is transmitted to data processor 120.

In a specific embodiment of the present invention, data processor 120 is capable of receiving data 105 as input data from temperature detection system 110 and processing data 105 to control the operation of heat generating system 130 and/or to display information to the user via a graphical user interface (GUI) 250. Some of the information displayed to the user using GUI 250 may include images displaying the temperature of a portion of target 140, the structure of a portion of target 140, the dead and dying cells in a portion of target 140 (where target 140 is biological tissue), and the like. Other information displayed may include the status of heat generating system 130, the temperature history of one or more points, areas, contours, planes, or volumes of a portion of target 140, etc. In one embodiment, data processor 120 also is capable of accepting user-defined parameters input through GUI 250. For example, a user may be capable of using a contrast adjuster on GUI 250 to change the contrast of an image, or to select points, areas, planes, or volumes of a portion of target 140 for monitoring of temperatures or tissue damage.

Data processor 120 processes data 105 using control strategy 127 to produce control parameters that direct the behavior of heat generating system 130. In one embodiment, heat generating system 130 receives and implements the control parameters from data processor 120 to perform the desired action. For example, data processor 120 may determine, using control strategy 127 and data 105, that the temperature of a portion of target 140 is exceeding a desired maximum temperature. In this example, data processor 120 may develop and send heating system parameter set 135 to heat generating system 130 that direct heat generating system 130 to lessen the intensity and/or duration of heat output. Heat generating system 130, upon receiving the heating system parameter set 135, modifies its heat energy output as directed. It will be appreciated that the term "intensity", as used herein, may refer to the relative instantaneous output, or the term may refer to the measure of the fraction of a cycle that heat generating system 130 is outputting energy, such as a duty cycle.

In at least one embodiment, energy delivery system 100 continuously or periodically measures a temperature distribution and/or a tissue damage distribution of a select portion of target 140 and processes the measurements (data 105) for feedback used in controlling the behavior of heat generating system 130 on a real-time, or near real-time basis. It will be appreciated that the periodic measurement of the select portion of target 140 may include measurements taken on a fixed frequency, intermittently, randomly, as directed by a user, and the like. It will also be appreciated that the term "real-time", as used herein, refers to the ability of energy delivery system 100 to measure and process data obtained from a select portion of target 140 and control the output of heat generating system 130 in a manner fast enough so that undesired results occurring to target 140 are minimized before being detected. For example, if temperature detection system 110 and data processor 120 capture and process data every ten seconds for real time operation, the heat output of heat generating system 130 should be limited such that undesired results, such as healthy tissue damage, tissue charring, and the like, are unlikely to occur between the ten second data capturing and processing cycle. Similarly, in at least one embodiment, the term "near real time" refers to the ability of energy delivery system 100 to affect control before significant undesired results occur in target 140.

The degree to which energy delivery system 100 approximates real-time feedback may be dependent on one or more of the following: the speed in which temperature detection system 110 is capable of measuring with a desired accuracy a portion of target 140; the size, shape, and/or resolution of the measured portion of target 140; the data transfer rate between temperature detection system 110 and data processor 120; the speed at which data processor 120 is capable of processing data 105 received from temperature detection system 110, producing control parameters for heat generating system 130, and producing images and information on GUI 250 for the user; the speed at which heat generating system 130 is capable of responding and producing the desired outcome of the heating system parameter set 135 transmitted from data processor 120; and the data transfer rate between data processor 120 and heat generating device 130. The desired resolution of the images representative of characteristics of the measured portion of target 140 may also affect the real-time capacity of energy delivery system 100. For example, an image with a higher signal-to-noise ratio (SNR) may take longer to measure and/or process than an image with a lower SNR. The desired SNR may be defined by the user, the limitations of the hardware and/or software of energy delivery system 100, etc.

Figure 2:
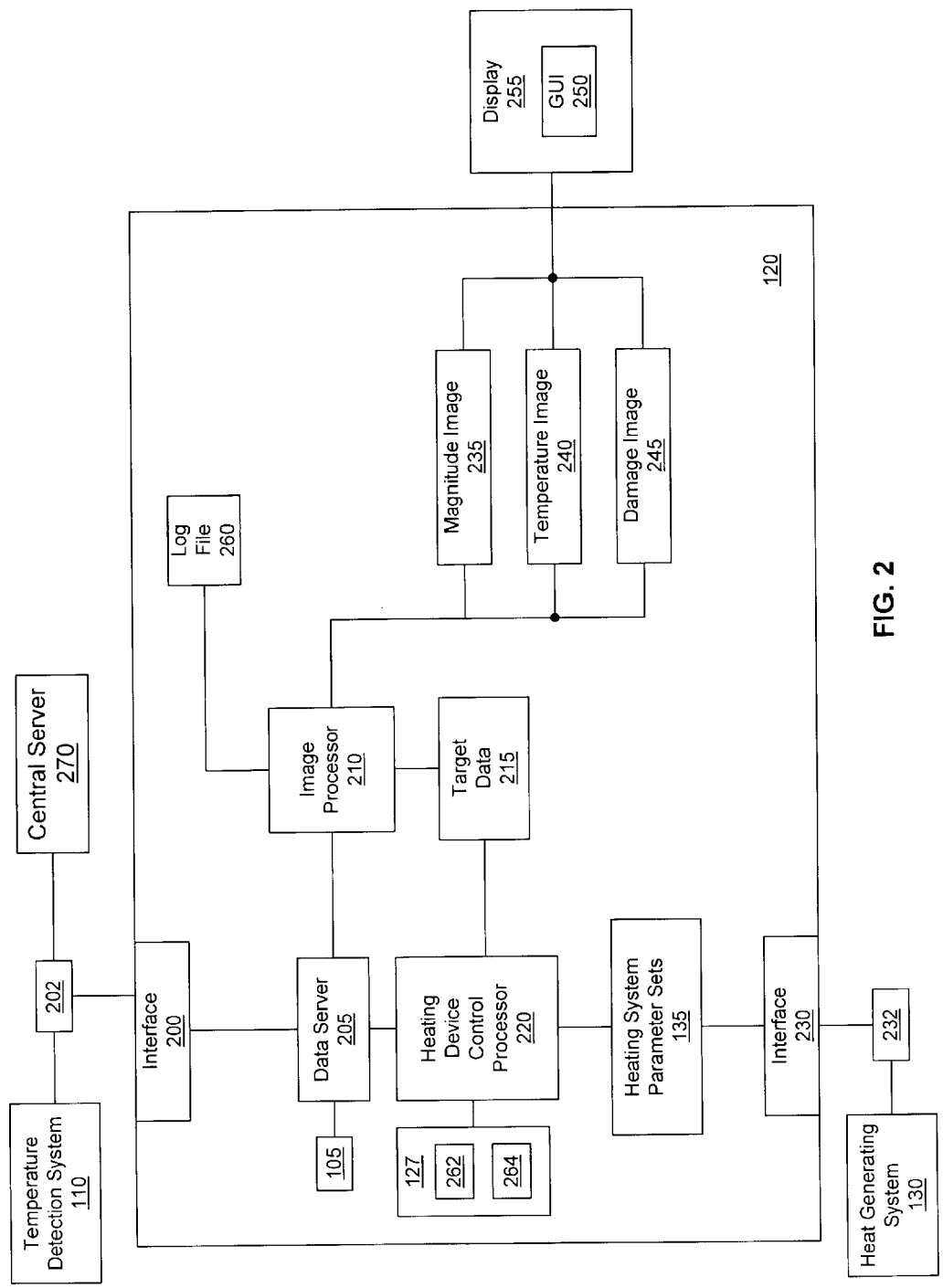
FIG. 2 is a diagram illustrating a data processor according to at least one embodiment of the present invention.

Referring next to FIG. 2, data processor 120 is illustrated in greater detail, according to at least one embodiment of the present invention. Reference numerals in FIG. 2 that are common to reference numerals in FIG. 1 indicate like, similar or identical features or elements. Data processor 120 includes thermal detection system interface 200, data route 202, image processor 210, heating device control processor 220, heating device system interface 230, control route 232, and connections to graphical user interface (GUI) 250 implemented using display 255. In one embodiment, data processor 120 further includes data server 205 and/or log file 260. It will be appreciated that one or more elements of data processor 120 may be physically or logically located on one or more processing devices. It will also be appreciated that one or more elements of data processor 120 may be physically or logically located on temperature detection system 110 or heat generating system 130 without departing from the spirit or scope of the present invention. In addition, one or more of the elements illustrated in FIG. 2 can be implemented in software or firmware.

It should be understood that the specific steps indicated in the methods herein, and/or the functions of specific systems herein, may generally be implemented in hardware and/or software. For example, a specific step or function may be performed using software and/or firmware executed on one or more processing systems.

Typically, a system for processing of data associated with temperature measurements will include generic or specific processors. The processors can be based on a single processing device or a plurality of processing devices. Such a processing device may be a microprocessor, a microcontroller, a digital processor, a microcomputer, a portion of a central processing unit, a state machine, logic circuitry, and/or any device that manipulates the data.

The manipulation of the data is generally based upon operational instructions represented in a memory. The memory may be a single memory device or a plurality of memory devices. Such a memory device (machine readable media) may be a read only memory, a random access memory, a floppy disk memory, magnetic tape memory, erasable memory, a portion of a system memory, any other device that stores operational instructions in a digital format. Note that when the processor implements one or more of its functions, it may do so where the memory storing in the corresponding operational instructions is embedded within the circuitry comprising a state machine and/or other logic circuitry.

In at least one embodiment of the present invention, data processor 120 continuously or periodically receives data 105 collected by temperature detection system 110 as it becomes available-and processes data 105 to provide real-time feedback control of heat generating system 130. In one embodiment, data 105 is transmitted from temperature detection system 110 to data server 205 via temperature detection system interface 200 and data route 202. When temperature detection system 110 is local to data processor 120, data route 202 may include a serial connection, a parallel connection, an infrared connection, a wireless connection (such as a radio frequency or microwave connection), a point-to-point connection, and the like. In implementations where temperature detection system 110 is remote to data processor 120, data route 202 may include an Ethernet connection, a modem connection, a digital subscriber line connection, a satellite connection, etc. Accordingly, temperature detection system interface 200 includes an input/output interface compatible with data route 202. For example, if data route 202 is an Ethernet network, temperature detection system interface 200 could include an Ethernet card. In at least one embodiment, temperature detection system interface 200 includes a point-to-point interface, such as a RS-232 interface, an IEEE-488 interface, a digital I/O interface, and the like.

It will be understood that data 105 is to be transmitted, relayed, or communicated across data route 202 by means or protocols appropriate to the particular data route 202 and interface 200 employed in a particular embodiment. For example, when an Ethernet network is used, it is likely that data 105 will be transmitted over data route 202 using a Transmission Control Protocol (TCP) over an Internet Protocol (IP), or, more commonly, TCP/IP. These standardized data communication protocols are commonly in use on Ethernet networks, and their details are at least partially specified in Defense Advanced Research Projects Agency (DARPA) documents RFC793 and RFC791, respectively. It will also be appreciated that additional communications protocols may be used instead of or on top of the TCP/IP layers. For example, the UNIX network file sharing (NFS) protocol, the details of which are at least partially specified in Network Working Group document RFC 1094, may be used to transfer data 105 across data route 202 when also using an Ethernet network and TCP/IP protocol. The File Transfer Protocol (FTP), the details of which are at least partially specified in Network Working Group document RFC959, may also be used with data 105 transmitted over data route 202. The NetBIOS protocol, the details of which are at least partially specified in documents RFC1001 and RFC1002 and IEEE802.2 can similarly be used, as can its relatives including the server message block (SMB) protocol common to Microsoft Windows networks. Similarly, the Apple Talk or Apple Filing Protocol File Sharing (afpfs) protocols may be used to transfer data 105 over data route 202. Besides TCP/IP, other networking protocols may be used including, for example, Internetworking Packet Exchange/Sequential Packet Exchange (IPX/SPX). It is meant to be recognized that the foregoing in no way limit the implementation with which data route may be realized, and other realizations which are known to those of ordinary skill in the art are also within the scope of the invention. For example "wireless" networking protocols such as those specified in IEEE 802.11a and/or 802.11b may be used.

In one embodiment, data 105 is stored on temperature detection system 110 until retrieved by data processor 120. Data processor 120 may either poll temperature detection system 110 for updated data 105, or temperature detection system 110 may signal data processor 120 that updated data 105 is ready for retrieval. One method of polling is to use the creation of a file as a signal. For example, temperature detection system 110 can use a UNIX file system to store data 105 in a file data_file.dat. When temperature detection system 110 has completed the measurement of target 140 and stored all measured data 105 for a given cycle in data_file.dat, temperature detection system 110 creates a file data.new. Data processor 120 periodically checks for the existence of the file data.new. After temperature detection system 110 creates the file data.new and it is detected by data processor 120, data processor 120 may then download the file data_file.dat. After data processor 120 has downloaded data_file.dat, data processor 120 erases the file data.new, and temperature detection system 110 may then start storing data for the next control cycle in data_file.dat.

An alternate method of polling is to use a file system and semaphores for mutual exclusion. For example, temperature detection system 110 and data processor 120 may make use of a UNIX file system to store data 105 in a file temp_data.001, and use a semaphore associated with this file. When temperature detection system 110 is updating data 105, it places a mutual exclusion lock using the semaphore on the temp_data.001 file and begins to store updated data 105 in the temp_data.001 file. Once temperature detection system 110 is finished storing data 105 in the temp_data.001 file, it releases, or unlocks, its mutual exclusion lock on temp_data.001. Data processor 120 continuously attempts to place a mutual exclusion lock using the semaphore associated with the temp_data.001 file. When temperature detection system 110 releases its mutual exclusion lock, data processor 120 is then capable of placing its own lock on temp_data.001 and begins to download the data in the temp_data.001. When data processor 120 is finished downloading data 105, it releases its lock on the temp_data.001 file, and temperature detection system 110 may begin to store newly updated data 105 in temp_data.001 for the next cycle, and so on. It will be appreciated that other methods of retrieving data 105 from temperature detection system 110 may be used, such as interprocess communication (IPC). IPC generally refers to the data exchange between one process and another, either within the same processor or over a network. EPC is often accomplished using a transmission protocol that guarantees a response to a request. Examples of IPC include UNIX sockets, OS/2 named pipes, etc. IPC often utilizes many types of system calls. For example, one or more Unix sockets could be opened up between temperature detection system 110 and data processor 120, and data 105 could be transmitted over data route 202 according to methods known to those skilled in the art. It will be appreciated that data 105 may be transferred all at once when temperature detection system 110 is finished capturing all of data 105 for one cycle, or data 105 may be continuously transmitted as it is captured.

In one embodiment, data 105 is transferred from temperature detection system 110 to central data server 270 accessible by at least one temperature detection system 110 and at least one data processor 120. Data processor 120 may then retrieve data 105 when data processor 120 is ready for it. Use of central data server 270 has the benefit of allowing more than one data processor 120 to access data 105 from temperature detection system 110, and more than one temperature detection system 110 may provide data 105 to data processor 120. For example, many hospitals use a digital imaging and communications in medicine (DICOM) protocol server (central data server 270) to centrally store images captured by medical imaging devices (temperature detecting system 110) and make those images accessible to a wide variety of users. The medical imaging devices may be locally or remotely connected to the DICOM protocol server using a network interface, such as an Ethernet interface or a point-to-point interface. In one embodiment, one or more elements of data processor 120 may also function as central data server 270.

In one embodiment, image processor 210 retrieves data 105 from data server 205 and processes data 105 to develop a plurality of images for display on GUI 250 implemented using display 255 and for further processing to construct heat generating system control parameters or characteristics that can be used to determine actual control parameters. In one embodiment, image processor 210 constructs one or more of magnitude image 235, temperature image 240, and damage image 245 for each cycle of feedback in energy delivery system 100. Magnitude image 235, in at least one embodiment, includes an image representative of the physical structure of the measured portion of target 140. Temperature image 240 includes an image representative of the temperature mapping of the measured portion of target 140. Damage image 245 includes an image representative of an estimate of the location of biological tissue (target 140) that is dead or dying. Magnitude image 235, temperature image 240, and damage image 245 are formatted and displayed on display 255 using GUI 250. GUI 250 is discussed in further detail with reference to FIG. 4. In one embodiment, images 235, 240, and/or 245 are representative of a three-dimensional distribution of the structure, temperature, and/or damage. It will be appreciated that images 235, 240, and/or 245 may be black and white, grayscale, or color images. For example, different colors could represent different temperature ranges. In one embodiment, a plurality of images 235, 240, and/or 245 of different selection portions of target 140 may be displayed. The plurality of images 235, 240, and/or 245 may be displayed on a periodically alternating basis, or on demand as directed by a user.

As previously discussed, image processor 210 processes data 105 and/or images 235, 240, and 245 to produce target data 215 for heating device control processor 220. Target data 215 may include a temperature distribution, a damage distribution, structure information, and the like. Heating device control processor 220 uses target data 215 and control strategy 127 to produce heating system parameter set 135 for use in controlling heat generating system 130. Control strategy 127 uses one or more rule sets 262 and strategy parameter sets 264 to determine the desired operation of heat generating system 130. Rule set 262 includes an algorithm to determine the desired action of heat generating system 130 using target data 215 and at least one strategy parameter set 264. Strategy parameter set 264 may include parameters such as temperature membership values for lexical temperature values, damage membership values for lexical damage values, heat generating system 130 intensity levels, and the like. For example, one rule of rule set 262 may state that the heat source of heat generating system 130 is to be shut off if a maximum temperature (lexically defined by strategy parameter set 264 as "too hot") of a selected portion of target 140 is reached. In this example, analysis of target data 215 by heating device control processor 220 determines that the temperature of the portion of target 140 has exceeded the maximum temperature ("too hot"), so heating device control processor 220 produces, using control strategy 127, heating system parameter set 135 that will cause heat generating system 130 to shut off the heat source. In at least one embodiment, control strategy 127 includes fuzzy logic control and is discussed in greater detail with reference to FIGS. 5 and 6.

In at least one embodiment, after heating system parameter set 135 is produced by heating device control processor 220, it is transmitted to heat generating system 130 via heat generating system interface 230 and control route 232. When heat generating system 130 is local to data processor 120, control route 232 may include a serial connection, a parallel connection, an infrared connection, a wireless connection, a direct connection, such as a data bus or shared memory, and the like. In implementations where heat generating system 130 is remote to data processor 120, control route 232 may include an Ethernet connection, a modem connection, a digital subscriber line connection, a satellite connection, etc. Accordingly, heat generating system interface 230 includes an input/output interface compatible with control route 232. For example, if control route 232 is a serial cable, heat generating device interface 230 may include a serial input/output (I/O) card. In at least one embodiment, heat generating system interface 230 includes a point-to-point interface, such as a RS-232 interface, an IEEE-488 interface, a digital I/O interface, and the like.

Figure 3:
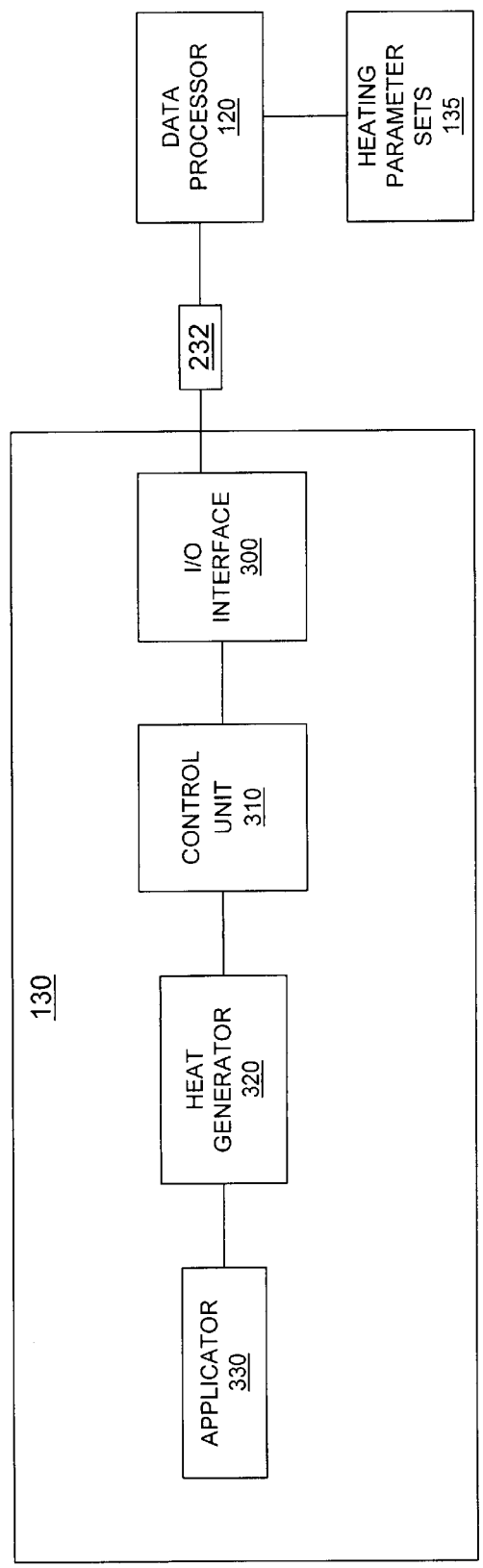
FIG. 3 is a diagram illustrating a heat generating system according to at least one embodiment of the present invention.

Referring next to FIG. 3, heat generating system 130 is illustrated in greater detail according to at least one embodiment of the present invention. Reference numerals in FIG. 3 that are common to reference numerals in FIGS. 1 and 2 indicate like, similar or identical features or elements. Heat generating system 130 includes input/output (I/O) interface 300, control unit 310, heat generator 320, and applicator 330. In at least one embodiment, heat generating system 130 receives heating system parameter set 135 (FIG. 2) from data processor 120 via I/O interface 300 and control route 232.

Control unit 310 processes heating system parameter set 135 transmitted from data processor 120 to control heat generator 320. For example, if heat generator 320 is a laser device, and heating system parameter set 135 indicates a specified laser intensity, duration, and/or duty cycle, control unit 310 produces the proper voltage and/or current for the proper duration and/or duty cycle to the laser device (heat generator 320) to cause the laser to have the specified intensity, duration, and/or duty cycle. In one embodiment, control unit 310 can monitor the operation of one or more elements of heat generating system 130 and transmits their statuses to data processor 120 via I/O interface 300 and control route 232. Data processor 120 may utilize the status of one or more elements of heat generating system 130 to modify control strategy 127 (FIG. 1).

Heat generator 320 is capable of producing heat or energy to be transformed into heat. In at least one embodiment, heat generator 320 is further capable of producing a varied intensity, duration, and/or duty cycle of energy based on input from control unit 310. Heat generator 320 can include, but is not limited to, a laser, a microwave device, a resistive heating element, a focused ultrasound device, an incoherent light device, a radio frequency (RF) probe, or other suitable application device. In an alternate embodiment, heat generator 320 includes a plurality of homogeneous or heterogeneous heat generating devices. For example, a laser device may be used in concert with a microwave device to deliver heat to target 140 (FIG. 1). The heat or energy produced by heat generator 320 is transmitted to target 140 via at least one applicator 330. Applicator 330 can include one or more optical fibers, one or more antennae, one or more transducers, and the like. For example, heat generator 320 may be implemented using a laser, and applicator 330 may be implemented as an optical fiber to deliver the energy produced by the laser into target 140. The optical fiber applicator may include one or more features known to those skilled in the art to produce desireable heating effects or patterns, including, but not limited to, an optically diffusive tip, or a specially shaped tip. In at least one embodiment, one or more applicators 330 may be used to create a spatial radiation pattern of heat energy. For example, multiple ultrasound transducers (heat generators 320 and applicators 330) may be implemented using phase delays to create a specific energy radiation pattern. It will be appreciated that in some implementations of the present invention, applicator 330 and heat generator 320 may be integrated into a single element. For example, a resistive wire placed in target 140 may act as both heat generator 320 and applicator 330 when a voltage potential is placed across the resistive wire.

Figure 4:
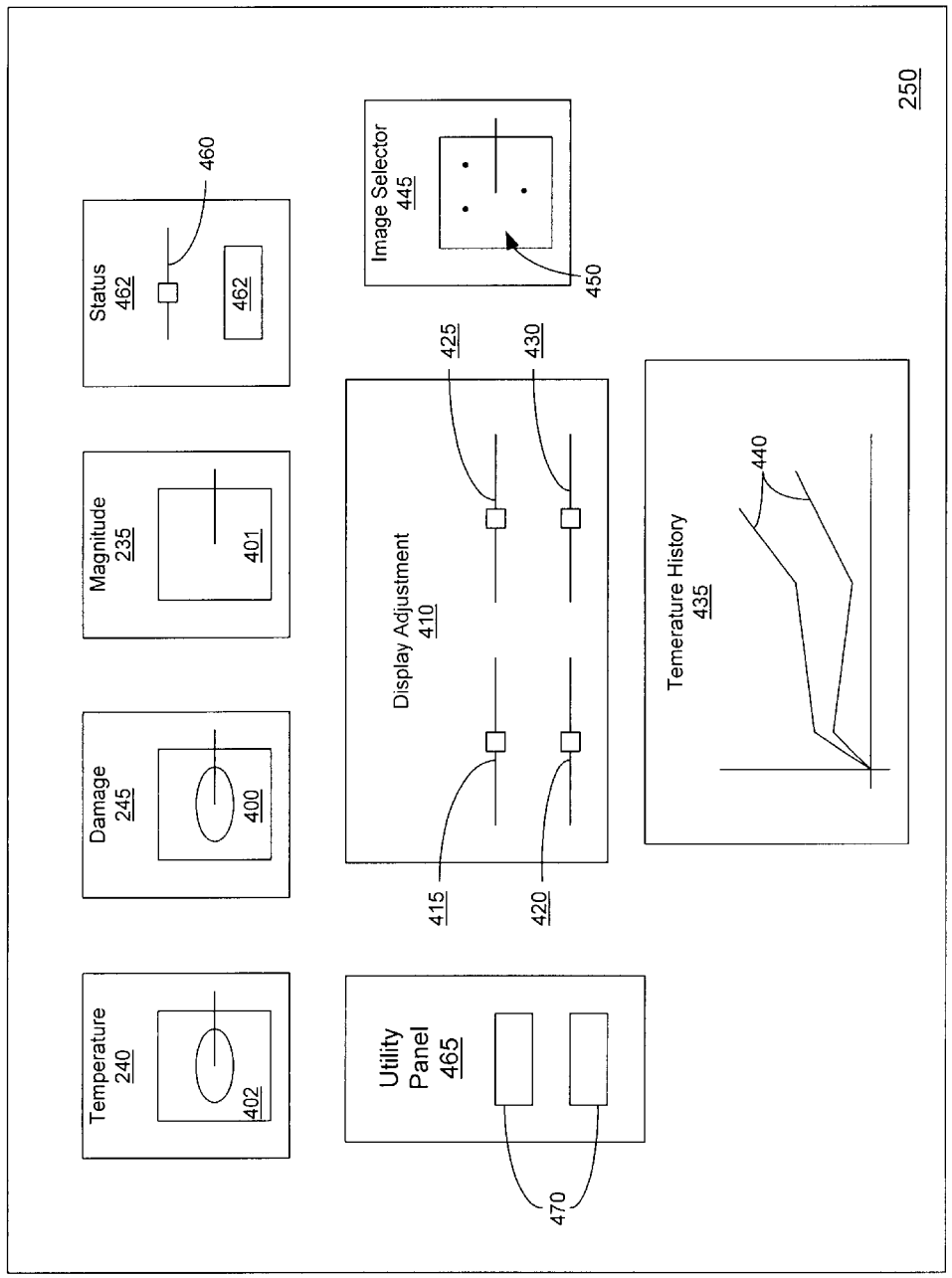
FIG. 4 is diagram illustrating a graphical user interface according to at least one embodiment of the present invention.

Referring next to FIG. 4, GUI 250 is illustrated in greater detail, according to at least one embodiment of the present invention. Reference numerals in FIG. 4 that are common to reference numerals in FIGS. 1–3 indicate like, similar or identical features or elements. In at least one embodiment, GUI 250 includes magnitude image 235, temperature image 240, damage image 245, image adjustment display 410, temperature history display 435, image selector 445, heating device status display 455, and utility panel display 465. It will be appreciated GUI 250 may further include one or more additional interactive displays without departing from the spirit and the scope of the present invention.

As discussed previously, magnitude image 235, temperature image 240, and damage image 245 can be derived from measurements of target 140 taken by temperature detection system 110 and transmitted to data processor 120 in the form of data 105 (FIG. 1). Magnitude image 235 displays an image representative of structure 401 of a selected portion of target 140 (FIG. 1) and temperature image 240 displays an image representative of temperature distribution 402 of a selected portion of target 140. In cases where target 140 is biological tissue, damage image 245 displays, in one embodiment, an image representative of cell damage region 400, which may be displayed alone or superimposed on either an image representative of temperature distribution 402 or an image representative of structure 401. In one embodiment, cell damage region 400 represents the portions of a selected portion of target 140 where cell death has occurred or is likely to occur as a result of the heat energy applied. Images 235, 240, and 245 may be a two-dimensional view representative of a selected section of target 140, such as a sagittal, coronal, axial section, or other arbitrary plane, or may be a three-dimensional view representative of a selected volume of target 140.

Image adjustment display 410 may be used to modify the display of images 235, 240, and/or 245 by GUI 250. Image adjustment display 410 includes contrast adjustment 415, brightness adjustment 420, color adjustment 425, and zoom adjustment 430. Contrast adjustment 415 adjusts the contrast of images 235, 240, and 245. Brightness adjustment 420 adjusts the brightness of images 235, 240, and 245. Color adjustment 245 adjusts the color properties when images 235, 240, and 245 are in color. Zoom adjustment 430 adjusts the magnification factor of images 235, 240, and 245 displayed. Adjustments 410, 415, 420, 425, and 430 may be modified through GUI 250 using a sliding knob, a turning dial, a value input field, or other methods known to those skilled in the art. It will be appreciated that additional image adjustments may be implemented without departing from the spirit and the scope of the present invention. For example, a user may strike the up and down arrow keys on a keyboard attached to data processor 120 to increase or decrease the zoom value of zoom adjustment 430.

In at least one embodiment, a user of energy delivery system 100 (FIG. 1) uses image selector 445 to select a portion of target 140 for monitoring and control. Image selector 445 includes, in one embodiment, structural image 235, but can also include temperature image 240 or damage image 245. Such image may be constructed from one set of MR data or from mathematical manipulation of one or more sets of MR data. The image may also comprise representation of one or more sets of MR data acquired previously. The user may select one or more image interest selections 450 for monitoring by energy delivery system 100 using an input device, such as a mouse, a touchpad, a touchscreen, a trackball, and the like. Image interest selections 450 may include individual points, areas, planes, or contours in implementations where the image (magnitude image 235, temperature image 240, or damage image 245) is displayed in two dimensions, or points, areas, contours, planes, or volumes in implementations where the image is displayed in three dimensions. In one embodiment, image interest selections 450 are associated with one or more membership sets, such as cold, medium, hot, and too hot temperature sets, or healthy, dying, and dead cell sets, and the like. Image interest selections 450 are input by GUI 250 to data processor 120 as elements of a strategy parameter set for use in controlling the operation of heat generating system 130. Membership sets and strategy parameter sets are discussed in greater detail with respect to FIG. 5.

As described previously, the user may use continuously or periodically updated temperature image 240, damage image 245, and magnitude image 235 to select image interest selections 450 in image selector 445 of GUI 250 (FIG. 4). In one embodiment, the image displayed in image selector 445 may include temperature image 240, damage image 245, magnitude image 235, or a combination thereof. For example, a combination image of temperature image 240 and damage image 245 may be displayed in image selector 445. In this example, the temperature distribution could be represented by pixels with a color spectrum between blue and red, and cells considered dead or dying could be represented by pixels with a white color. If image selector display is a two dimensional image, the user could select, using an input device such as a trackball, one or more points or contours (image interest selections 450) for data processor 120 to monitor and use in control strategy 127 (FIG. 2). These points could be associated with a temperature membership or cell damage membership, as discussed in greater detail with reference to FIGS. 5 and 6. Additionally, in at least one embodiment, multiple images representative of the structure, temperature distribution and/or damage distribution of different areas, planes, or volumes of a plurality of selected portions of target 140 may be displayed. The different areas, planes, or volumes of the selected portions may be parallel or perpendicular to each other, or they may be oriented at any angle to one another. One or more of the plurality of images may be displayed simultaneously, or groups of one or more may be displayed sequentially. The selection of the desired areas, planes, and/or volumes and display of the plurality of images representative of the areas, planes, and/or volumes may occur on a periodic basis or may be initiated and directed by the user. The selection and display of the images may also be determined by data processor 120 or temperature detection system 110 based on characteristics of the selection portion of target 140, such as the locations of the hottest temperature or the area with the greatest damage.

In at least one embodiment, the user-selected image interest selections 450 can be used to provide feedback to temperature detection system 110. For example, a user may select one or more of the hottest points and have temperature detection system 110 monitor the temperature of these points more frequently than the rest. In one embodiment, either temperature detection system 110 or data processor 120 is capable of automatically adjusting the monitoring of a selected portion of target 140 based on image interest selections 450. For example, suppose a user selects an area of target 140 to be monitored and data processor 120 determines that the upper half of the selected area has no appreciable temperature change, or the temperature distribution of the upper half is well within the acceptable temperature limits. In this example, it is determined that the bottom edge of the selected area is approaching a user-defined critical temperature. In this case, data processor 120 may instruct temperature detection system 110 to alter the area being monitored, and place the bottom edge of the previously monitored area in the center of the newly monitored area. This action would allow the user and data processor 120 to monitor the critical areas of the selected portion of target 140 by readjusting the image to focus on areas of interest. Likewise, in addition to shifting the area, plane, or volume of interest, data processor 120 may instruct temperature system 110 to change to an entirely different area, plane, or volume of interest in order to more accurately monitor critical features.

Temperature history display 435 includes one or more temperature history plots 440 associated with the one or more image interest selections 450. Temperature history plots 440 can be plots of the temperature of the associated image interest selection 450 as a function of time. It will be appreciated that one or more temperature history plots 440 may be illustrated on a single plot display with a common axis, on a separate plot display for each temperature history plot 440, or a combination thereof. In cases where image interest selections 450 are not single points, such as a plane or a volume, it will be appreciated that temperature history plot 440 may consist of an average temperature history, a temperature history of a single hottest point, etc.

In at least one embodiment, heating device status display 455 is capable of displaying information regarding the status of heat generating system 130. In one embodiment, heating device status display 455 includes intensity indicator 460. Intensity indicator 460 displays the intensity of heat output of heat generating system 130. The intensity may be displayed as a relative percent, such as 0 to 100% of heating capacity, as an actual measurement, such as 0 to 5 Watts, as a graph representative of the duty cycle, or as another physical quantity as may be appropriate to the heat generation method employed. Heating device status display 455 may also include emergency shut off button 462 capable of turning off the energy output of heat generating system 130. For example, a user may determine that a portion of target 140 has exceeded a desired maximum temperature. The user may then activate emergency shutoff button 462 to prevent or stop any damage to target 140. It will be appreciated that heating device status display 455 may also display additional information, such as time in use, total power output, and the like. In one embodiment, utility panel display 465 is capable of executing utility programs and processes using one or more buttons 470. Utility programs and processes can include startup and shutdown processes, add/remove display processes, data saving processes, GUI setup processes, and the like.

Figure 5:
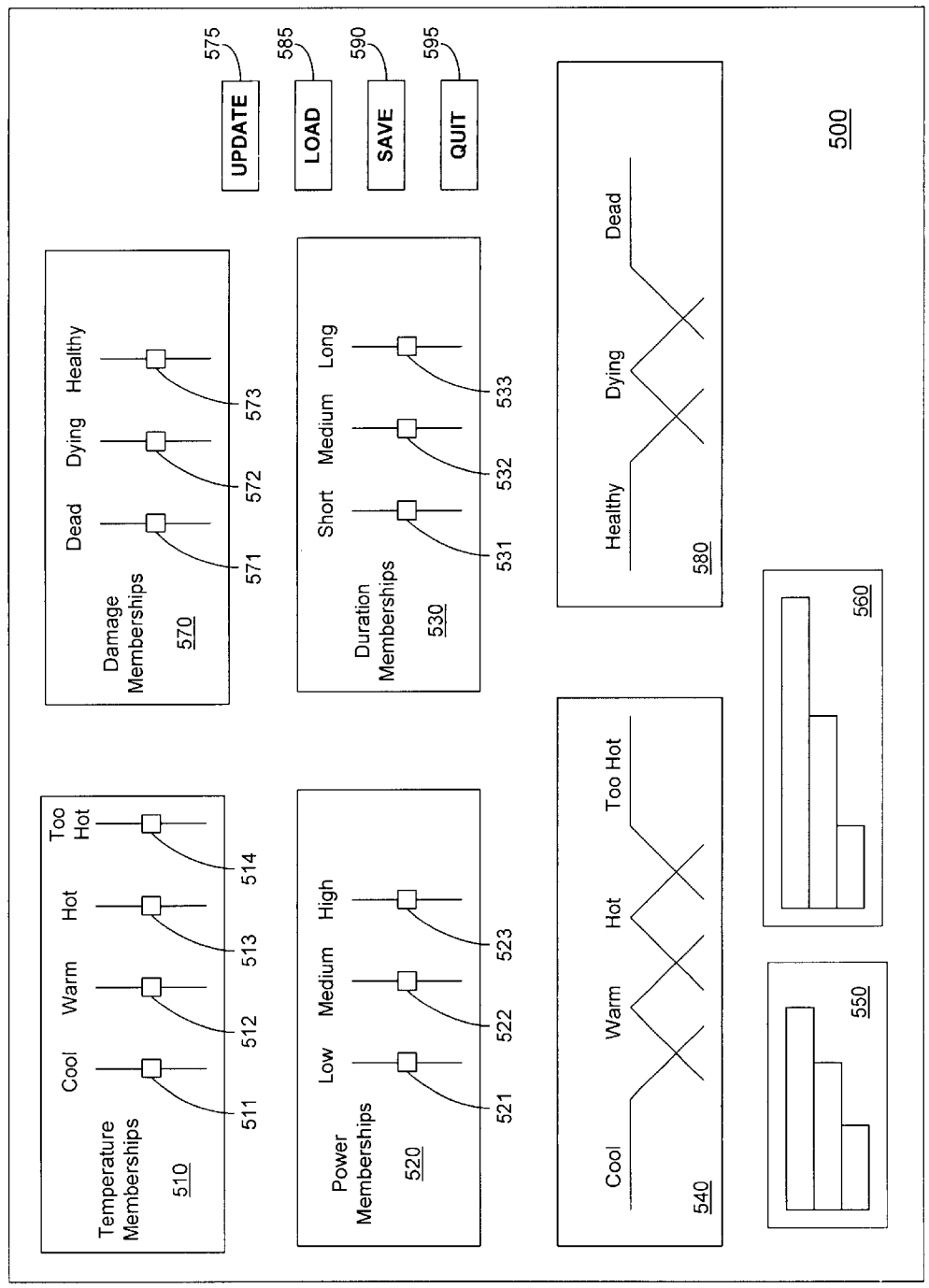
FIG. 5 is a diagram illustrating a fuzzy logic membership tuning interface according to at least one embodiment of the present invention.

Referring now to FIG. 5, fuzzy logic membership tuning interface 500 is illustrated according to at least one embodiment of the present invention. Reference numerals in FIG. 5 that are common to reference numerals in FIGS. 1–4 indicate like, similar or identical features or elements. Fuzzy logic membership tuning interface 500, herein referred to as membership tuning interface 500, includes temperature membership group 510, heating device power membership group 520, duration membership group 530, temperature display 540, power display 550, duration display 560, quit button 595, load button 585, save button 590, and update button 575. In one embodiment, tuning interface 500 is accessed by when a user selects one of buttons 470 in utility panel display 465 (FIG. 4). In implementations where energy delivery system 100 (FIG. 1) is used to produce lesions in biological tissue (target 140), membership tuning interface 500 further includes damage membership group 570 and damage display 580. It will be appreciated that membership tuning interface 500 may include other membership groups with out departing from the spirit and the scope of the present invention.

As discussed previously, heating device control processor 220 (FIG. 2) uses control strategy 127, one or more rule sets 262, and one or more strategy parameter sets 264 to control the energy output of heat generating system 130. In one embodiment, a user employs membership tuning interface 500 to input user-preferred parameters into one or more strategy parameter sets 262. In one embodiment, a user may modify four types of memberships: temperature, tissue damage, heating device power, and heating device output duration. Temperature membership group 510 is capable of setting membership values for cool temperature membership 511, warm membership 512, hot membership 513, and too hot membership 514. Heating device power membership group 520 is capable of setting membership values for low membership 521, medium membership 522, and high membership 523. Duration membership group 530 is capable of setting membership values for short membership 531, medium membership 532, and long membership 533. Damage membership group 570 is capable of setting membership values for dead membership group 571, dying membership group 572, and healthy membership group 573. The user may modify the values of each membership by use of a sliding knob, a turning dial, a numerical input box, and the like.

Temperature display 540, damage display 580, power display 550, and duration display 560 are capable of visually displaying the relationships between their associated membership groups (temperature membership group 510, damage membership group 570, heating device power membership group 520, and duration membership group 530, respectively). As a user modifies the values for a given membership, the associated membership display dynamically updates to reflect the new membership group composition. For example, an increase in the value of cool membership 511 updates the graph representing cool membership 511 in temperature graph 540. It will be appreciated that various types of charts and graphs may be used to display membership groups 510, 520, 530, and 570, such as line graphs, bar graphs, pie charts, etc. Additionally, in one embodiment, temperature display 540, and the associated values for memberships 510, 520, 530, and 570 may be adjusted by direct manipulation of temperature display 540 and/or damage display 580 by the user. For example, a user could use a mouse to click on one of the graph lines for cool membership 511 and drag and position the graph line into the desired location, and thereby dynamically altering the values and distribution of cool membership 511. It will be appreciated that a specific membership value and distribution may be modified separately from the other associated memberships, or memberships may be adjusted in relation to one another.

When a user is satisfied with the results of modification of the values of the memberships, the user may save, load, and/or update these values. Save button 590 is capable of saving the displayed membership values in a file, database, and the like. For example, a user may set up membership values for a specific tissue (target 140) type and select save button 590 to save the setup in a file. Load button 585 is capable, when selected, of loading and displaying membership values previously saved in a file or database. Update button 575 is capable of dynamically updating membership values that are in strategy parameter set 262 that is currently being used by heating device control processor 220. By selecting update button 575, the user dynamically modifies the parameters used by data processor 120 to control heat generating system 130. When selected by the user, quit button 595 terminates membership tuning interface 500 without saving any changes to membership values made since the save button 590 was last selected. In at least one embodiment, membership tuning interface 500 is capable of evaluating strategy parameter set 264 before updating for safety reasons or to prevent unintended results.

Figure 6:
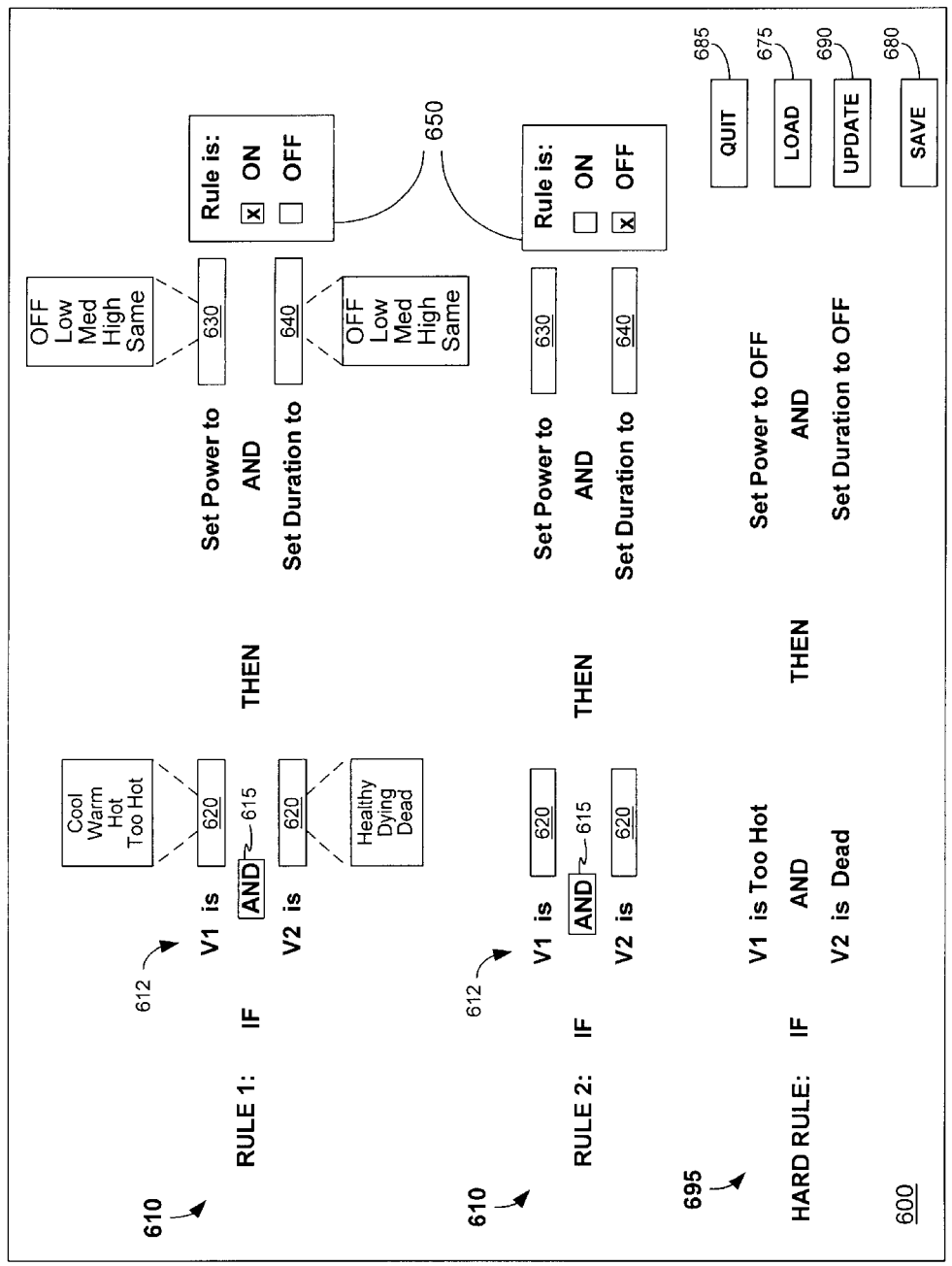
FIG. 6 is a diagram illustrating a fuzzy logic rule set tuning interface according to at least one embodiment of the present invention.

Referring now to FIG. 6, a fuzzy logic rule set tuning interface is illustrated according to one embodiment of the present invention. Reference numerals in FIG. 6 that are common to reference numerals in FIGS. 1–5 indicate like, similar or identical features or elements. Fuzzy logic rule set tuning interface 600, herein referred to as rule set tuning interface 600 includes one or more rules 610, one or more rule activation boxes 650, load button 675, save button 680, update button 690, and quit button 685. Rule 610 includes at least one control variable 612 associated with the temperature of a given location of target 140 and/or the cell damage of a given location of a biological tissue (target 140), one or more control membership fields 620, one or more power membership fields 630, and one or more duration membership fields 640. Rule 610 may further include one or more fuzzy logic operators 615. Rule activation box 650 includes an ON box and an OFF box.

In one embodiment of the present invention, rule set tuning interface 600 allows a user to construct and/or modify a fuzzy logic control strategy (an embodiment of control strategy 127), which in turn governs the feedback control process of energy delivery system 100 (FIG. 1). The user is capable of building one or more rules 610 combined into rule set 262 that govern the behavior of heat generating system 130 (FIG. 1) using if-then statements and fuzzy logic operators and variables. Using fuzzy logic control, the truthfulness of each variable of each premise (the "if" statement) is evaluated based on its membership to specific membership groups. The extent to which the conclusion (the "then" statement) is performed is based on the evaluated truthfulness of the premise. To construct each of at least one rule 610, the user selects control variable 612 corresponding to an image interest selection 450 (FIG. 4) selected using image selector 445 displayed on GUI 250. If more than one control variable 612 is selected for rule 610, the user also selects an operator for fuzzy logic operator 615. Fuzzy logic operators represented in fuzzy logic operator 615 may include, but are not limited to, AND, OR, NAND (NOT AND), NOR (NOT OR), or other fuzzy logic operators. Additionally, the user selects a lexical value for each control membership field 620 corresponding to the one or more control variables 612. In one embodiment, the lexical values for control membership field 620 include temperature lexical values of cool, warm, hot, and too hot. Lexical values for control membership field 620 may also include damage lexical values, such as healthy, dying, and dead. The user also selects a lexical value for power membership field 630 and duration membership field 640. In one embodiment, the lexical values for power membership field 630 include off, low, medium, high, and same, and the lexical values for duration membership field 640 include short, medium, long, and same. In one embodiment, the numerical equivalents of the lexical values of membership fields 620, 630, and 640 are determined by user input to tuning interface 600. It will be appreciated that the numerical equivalents may also be hard-coded into GUI 250, loaded from a database or a file, and the like.

In an alternate embodiment, a more traditional control methodology is used. For example, a software-based algorithm may be used for closed-loop control of the heat output of energy delivery system 100 (FIG. 1). Alternately, the control method may be hardwired into the hardware of data processor 120. The user may input user-defined parameters for these types of control methodologies in a manner similar to the one presented with reference to FIGS. 5 and 6. It will be appreciated that other control methods may be used without departing from the spirit and scope of the present invention.

In one embodiment, rule 610 implements fuzzy logic to define a response to a situation defined by control variables 612, fuzzy logic operator 615, control membership field 620, power membership field 630, and duration membership field 640. Fuzzy logic, as opposed to Boolean logic with absolute truth and absolute false, uses a range of values to represent the truthfulness or falseness of a variable. As a result, the truthfulness of a given statement using fuzzy logic can be represented as a probability. Using an if-then statement, rule 610 determines whether a statement of one or more temperature variables 612 is true using logical operator 612 to evaluate the degree of truthfulness. The values for corresponding power membership field 630 and duration membership field 640 are set according to the degree of truthfulness of the "if" statement of a fuzzy logic operation (logical operator 612) between two or more fuzzy logic variables (control membership fields 620). The power membership field 630 and duration membership field 640 values are implemented by heating device control processor 220 (FIG. 2) to create heating system parameter set 135 (FIG. 1). After heating system parameter set 135 is created, it is transmitted to heat generating system 130. Heat generating system 130 receives heating system parameter set 135 and modifies its heat output to match the parameters set by power membership field 630 and duration membership field 640.

A user also has the capability of shutting off a particular rule 610 using rule activation box 650. For example, if a user determines that one or more rules 610 are interfering with the correct operation of energy delivery system 100 (FIG. 1), the user may dynamically disable the interfering rules 610 by selecting the associated OFF box. Similarly, if the user wishes to enable a disabled rule 610, the user may select ON box to dynamically enable the associated rule 610.

In at least one embodiment of the present invention, rule set 262 further includes one or more hard rules 695. Hard rules 695 include rules used to limit the operating boundaries of heat generating system 130 for safety and/or device limitation reasons. For example, heat generating system 130 may include a diode laser that may have a maximum power setting that exceeds the maximum safe level. In this example, hard rules 695 would include rules that limit the power output of the laser to safe levels only. Hard rules 695, in one embodiment, supercede all user-defined rules 610, and normal users are not capable of modifying or disabling any hard rules 695. In one embodiment, rule set tuning interface 600 is capable of determining if a given rule 610 interferes with one or more hard rules 695. If a rule 610 does interfere, rule set tuning interface 600 is capable of disabling the interfering rule 610 by selecting the OFF box of associated rule activation box 650. It will be appreciated that hard rules 695 may be loaded from a file or database, input by an authorized administrator, etc. In an alternate embodiment, hard rules 695 are hardcoded into the software of data processor 120 or hardwired into the hardware of data processor 120. In this case, hard rules 695 may have been coded or implemented in hardware by the user or by the manufacturer, or a combination therein. Alternately, hard rules 695 may be implemented using data from image interest selections 450 (FIG. 4). For example, a user could pick a point at the source of the heat in target 140 and a point in an outlying area. In this case, the user could define a hard rule (hard rule 695) that prohibits the temperature of the point at the heat source from exceeding a user-defined temperature and similarly may set a maximum temperature for the outlying point.

In addition to creating rule sets 262 (FIG. 2), rule set tuning interface 600 is capable of saving created rule sets 262, or loading preexisting rule sets 262 from a file or database. Rule sets 262 may be saved by selecting save button 680, which is capable of saving rule sets 262 as a file or in a database. Preexisting rule sets 262 may be loaded by a user from a database or file by selecting load button 675. Update button 690 is capable of dynamically updating rule set 262 currently used by control strategy 127 to govern the operation of heat generating system 130 (FIG. 1). In the event that a user desires to terminate rule set tuning interface 600 without saving any changes to a given rule set 262, the user can select quit button 685. Additionally, rules 610 for rule set 262 used by control strategy 127 and heating device control processor 220 (FIG. 2) may dynamically be updated during operation by using update button 690.

Figure 7:
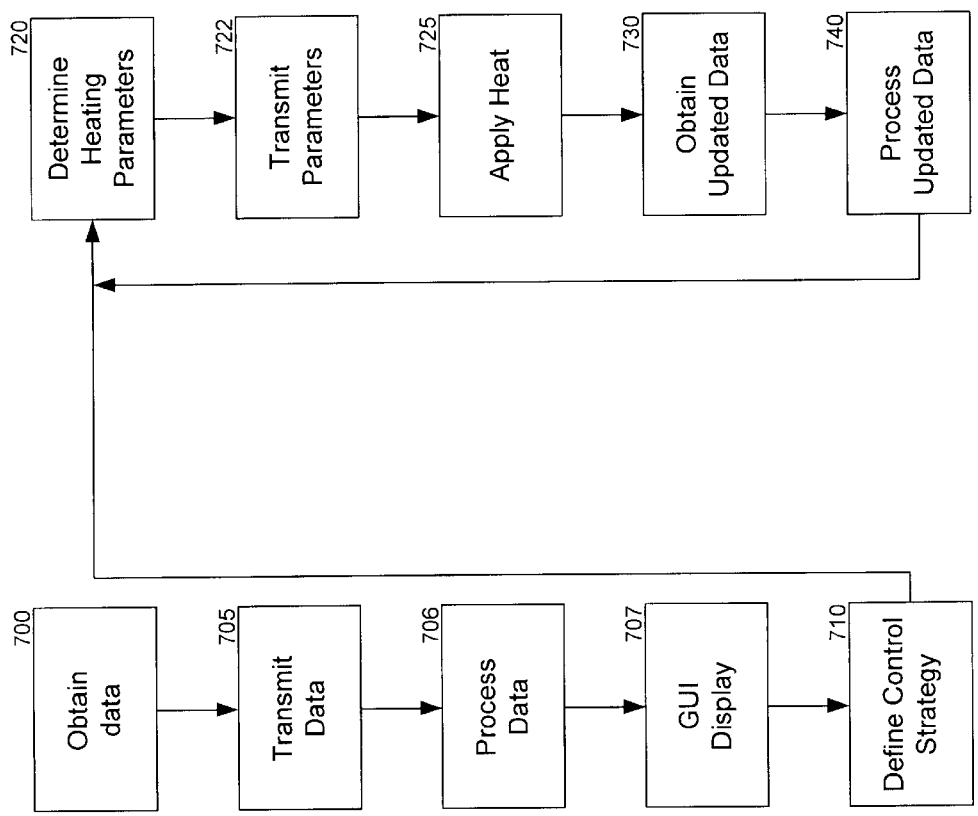
FIG. 7 is a flow diagram illustrating a method for real-time feedback control of an energy delivery system according to at least one embodiment of the present invention.

Referring next to FIG. 7, a method for utilizing real-time, or near real-time, feedback to control an energy delivery system is discussed according to one embodiment of the present invention. Reference numerals in FIG. 7 that are common to reference numerals in FIGS. 1–6 indicate like, similar or identical features or elements. In step 700, temperature detection system 110 (FIG. 1) obtains data 105 from measurements conducted on target 140 for use as initial reference data for data processor 120. This initial reference data may be utilized to develop an initial image representing magnitude image 235, temperature image 240, and damage image 245 (FIG. 2). The initial reference data may also be used to develop an initial reference temperature distribution in implementations where temperature detection system 110 is only capable of detecting temperature differences, rather than absolute temperature.

In step 705, initial data 105 is transmitted from temperature detection system 110 to data processor 120 (FIG. 2). Data 105 may be stored in a database on temperature detection system 110, transmitted immediately after the data capture cycle is completed, transmitted to central data server 270, or transmitted continuously as data 105 is captured. In step 706, data 105 received from temperature detection system 110 is processed by data processor 120. Data 105 is used by image processor 210 (FIG. 2) to develop magnitude image 235, temperature image 240, and damage image 245 for display by GUI 250. In addition, data processor 120 uses data 105 to initiate control of the heat output of heat generating system 130, as described previously. In step 707, data 105 is used by GUI 250 (FIG. 2) to display the initial images for magnitude image 235, temperature image 240, and damage image 245. As no heat has been applied to target 140 when initial data 105 was measured, damage image 245 and temperature image 240 have no temperature or damage related information to display. Similarly, temperature history 435 (FIG. 4) does not have any information to display yet. A user may use the information presented in the images to determine and input user-defined parameters.

One or more image interest selections 450 (FIG. 4), one or more rule sets 262 (FIG. 2) and strategy parameter sets 264 used to develop control strategy 127 (FIG. 1) are input to data processor 120 via GUI 250 (FIG. 2) by a user in step 710. As discussed previously, the user may select one or more points, contours, areas, planes, or volumes of interest for monitoring using an input device in image selector 445. The user may select the one or more image interest selections 450 using an input device, such as a mouse, touch screen, trackball, etc. Alternatively, image interest selections may be predetermined using data from a file or database.

In at least one embodiment, control strategy 127 is implemented using membership tuning interface 500 (FIG. 5) and rule set tuning interface 600 (FIG. 6) to set the values of strategy parameter set 264 and one or more rule sets 262 (FIG. 2). The user may define strategy parameter set 264, in at least one embodiment, by entering or modifying values for memberships groups 510, 520, 530, and 570 (FIG. 5). The inputted values may be determined using past experience as a guide, a standardized table of values, and/or by loading a previously constructed strategy parameter set 264 from a file or a database as described previously. Similarly, one or more rule sets 262 may be input by the user based on experience, tables, or by loading previously constructed rules sets 262 from a file or database.

In step 720, data processor 120 uses control strategy 127 developed in step 710 and information extracted from data 105 obtained by temperature detection system 110 to construct heating system parameter set 135 (FIG. 1). Heating system parameter set 135 is used to govern the behavior of heat generating system 130. Heating system parameter set 135 is generated by heating device control processor 220 by using temperature data extracted from data 105, and/or cell damage data calculated from data 105 if target 140 (FIG. 1) includes biological tissue. For example, one rule set 610 (FIG. 6) states that heat generating system 130 is to be shut off (power membership field 630 value set to off) if the temperature of a given image interest selection 450 (control variable 612) is too hot (control membership field 620 set to too hot). In this example, heating device control processor 220 would construct heating system parameter set 135 in a way that would shut of heat generating system 130 when it received and enacted heating system parameter set 135.

In step 722, heating system parameter set 135 is transmitted to heat generating system 130. In one embodiment, heat generating system 130 is local to data processor 120. In this case, heating system parameter set 135 may be transmitted from data processor 120 to heat generating system 130 using a direct connection, such as shared memory, a serial connection, a parallel connection, universal serial bus connection, and the like. In another embodiment, heat generating system 130 is remotely connected to data processor 120. In this implementation, data processor 120 and heat generating system 130 may be connected by a microwave connection, a satellite link, by Ethernet, by telephone modem, and the like. In either embodiment, heating system parameter set 135 is received by heat generating system 130 and processed to produce the desired heat output. In one embodiment, heat generating system 130 is capable of transmitting an error signal to data processor 120 if heat generating system 130 is unable to perform as directed by heating system parameter set 135. Data processor 120 may then take the error signal into account when constructing subsequent heating system parameter set 135 for the next cycle.

In step 730, the next cycle of data 105 is collected by temperature detection system 110. Temperature detection system 110 (FIG. 2) obtains data 105 from measurements conducted on target 140 for processing by data processor 120. In step 735, data is transmitted to data processor 120 as discussed with reference to step 705. In step 740, data 105 received from temperature detection system 110 is processed by data processor 120. Data 105 is used by image processor 210 (FIG. 2) to develop updated images of magnitude image 235, temperature image 240, and damage image 245 for display by GUI 250. In one embodiment, the initial reference data collected in step 700 is used in conjunction with data 105 obtained in the current cycle to develop an updated temperature image 240 and damage image 245 in implementations where temperature detection system 110 is only capable of detecting temperature differences, rather than absolute temperature. Additionally, data 105 is processed by image processor 210 to produce target data 215 (FIG. 2) for the next cycle of the real-time closed loop feedback control. Steps 720 through 740 are continuously repeated until the user terminates the process, or data processor 120 determines that termination is necessary for safety or other reasons. For example, the temperature of a image interest selection 450 (FIG. 4) selected by the user may have exceeded the desired maximum temperature as defined by strategy parameter set 264 and rule set 262 (FIG. 2). In this situation, data processor 120 would terminate the heat output of heat generating system 130, and may notify the user of the impending shut down.

Figure 8:
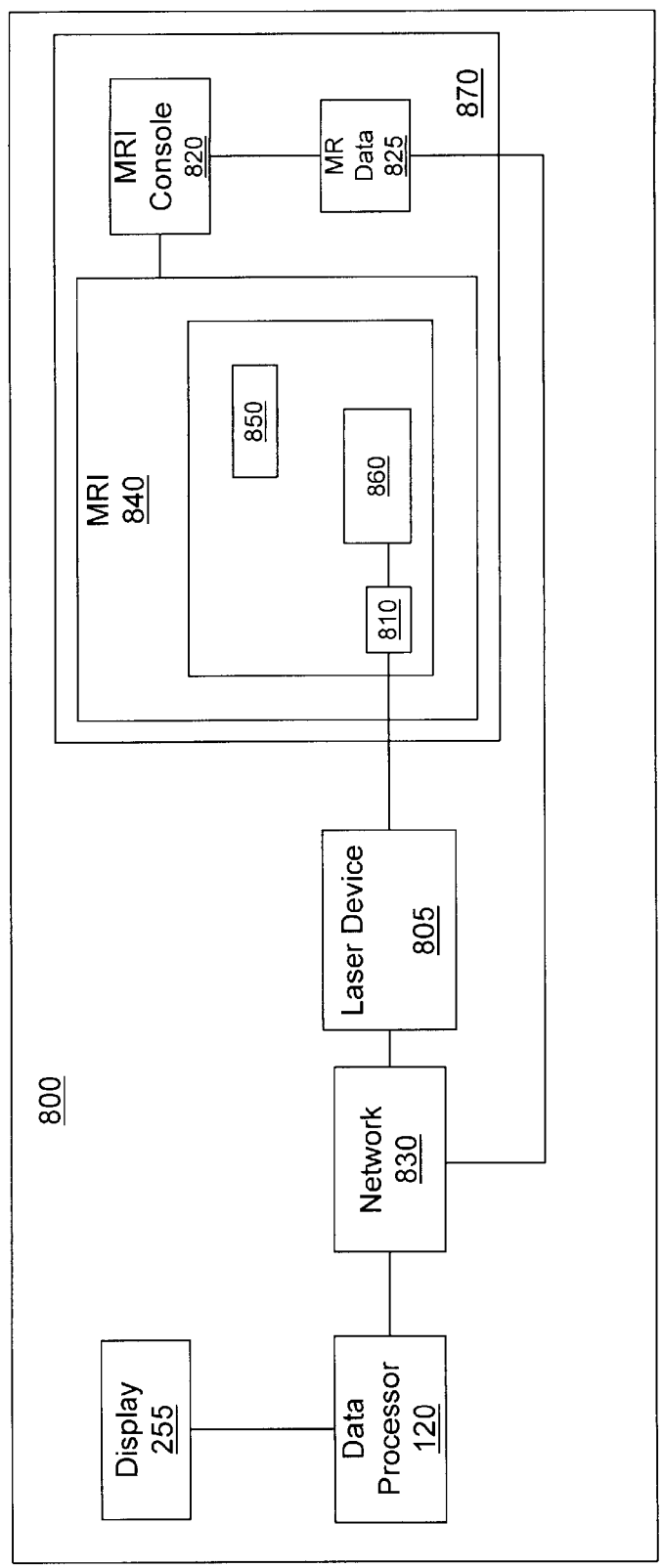
FIG. 8 is a diagram illustrating an implementation of an energy delivery system according to at least one embodiment of the present invention.

Referring next to FIG. 8, a magnetic resonance guided laser energy thermal therapy system is illustrated according to one embodiment of the present invention. Reference numerals in FIG. 8 that are common to reference numerals in FIGS. 1–7 indicate like, similar or identical features or elements. Magnetic resonance guided laser energy thermal therapy system 800, herein referred to as MR thermal therapy system 800, includes data processor 120, display 255, laser device 805 (an embodiment of heat generating system 130), optic fiber 810 (an embodiment of applicator 330), network 830, MR system 870 (an embodiment of temperature detection system 110), and tissue 860 (an embodiment of target 140). MR system 870 includes magnet 840, radio frequency (RF) coil 850, and MR console 820.

In one embodiment of the present invention, MR thermal therapy system 800 is used to produce lesions in biological tissue (tissue 860), such as muscle, organs, and the like. For example, MR thermal therapy system 800 may be used to cause cell necrosis in cancerous cells in a tumor, while leaving most or all of the healthy cells surrounding the tumor intact.

In one embodiment, data processor 120, discussed in greater detail with reference to FIG. 2, is connected to laser 805 and MR system 870 via network 830. Network 830 may include the Internet, a wireless network, a satellite network, and the like. One reason for a remote connection between data processor 120 and laser 805 and MR system 870 is that a doctor/practitioner may consult on the operation of MR thermal therapy system 200 from a remote location without having to be located near MR system 870 or laser 805. For example, MR thermal therapy system 800 could be transported to a difficult to access remote region by a technician, and an experienced doctor located elsewhere who is unable to reach the remote region could direct the actions of the technician, or control the system himself, based on the images displayed to the doctor by GUI 250 (FIG. 2) on display 255 connected to data processor 120. It will also be appreciated that laser 805 may be remotely located from tissue 860 with the laser energy delivered to tissue 860 via optic fiber 810.

MR system 870 continuously or periodically measures and stores data obtained by measurement conducted on tissue 860. One implementation of MR system 870 may be an imaging system equipped to generate proton resonance images. In this implementation, the system is capable of exhibiting a spatial-temperature resolution of $0.16°$ C.·cm or better. MR system 870 uses a magnetic field, created by magnet 840, and radio emissions, emitted from RF coil 850, to continuously obtain MR data 825 (data 105) from an area, plane, or volume of tissue 860. In one embodiment, MR data 825 includes a complex number for each pixel of an MR image obtained by MR console 820. For example, if MR data 825 includes the data for a 256 by 256 pixel resolution MR image, MR data 825 includes 65536 complex numbers. Because of the time involved in interrogating the selected portion of tissue 860 using magnetic resonance imaging techniques, MR system 870 is generally the limiting factor in the degree to which MR thermal therapy system 800 behaves in a real-time fashion. For example, in one implementation of MR thermal therapy system 800, MR system 870 takes an average of seventeen seconds to measure and collect MR data 825 on an MR image with a resolution of 256 by 256 pixels. It will be appreciated that as the signal-to-noise ratio of a desired MR image decreases, and/or as the measurement speed of MR system 870 for a given signal-to-noise ratio increases, the delay in real-time feedback control will be reduced.

MR data 825 is continuously updated and transmitted to data processor 120 for real-time, or near real-time, feedback control. Data processor 120 processes updated MR data 825 to generate images for GUI 250 and to control the output of laser 805. In one embodiment, data processor 120 performs Fourier transform decoding on MR data 825 to produce image data. In an alternate embodiment, MR system 870 processes MR data 825 to produce image data and transmits the image data to data processor 120 for further processing. For example, data processor 120 could perform a frequency domain analysis on MR data 825 and produce a complex number representative of each pixel of an image to be displayed on GUI 250. It will also be appreciated that the formatting of MR data 825 into image data could be performed by MR console 820. MR console 820 would then transmit the image data to data processor 120. The magnitudes of the pixels' values may be used to create magnitude image 235 (FIG. 2), which represents the physical structure of an area, cross-section or volume of tissue 860. In one embodiment, the physical structure of the area, cross-section, or volume is determined using the localized calculated spin density of hydrogen molecules measured by MR system 870. It will be appreciated by those skilled in the art that the MR image may be obtained using any of a number of techniques designed to elucidate the structure of the object being imaged. For example, so called "T1-weighted" or "T2-weighted" images may be obtained, where T1 and T2 refer to intrinsic magnetic resonance sensitive properties of all tissues, and weighted implies that the contrast of the image has been adjusted to exemplify local difference in a particular parameter. Additionally, it is well-known that certain magnetic resonance contrast agents may be administered prior to or during imaging. Such agents are preferentially deposited in tissues such as tumor and affect the local MR imaging environment in a way that makes the tumor easier to identify. Imaging methods such as gradient recalled echo (GRE) sequences may also be used to generate temperature sensitive images. As well, aforementioned T1-weighted images may be used to generate temperature sensitive images, as the T1 property of tissue is temperature-dependent. In at least one embodiment, a reference image is obtained before laser 805 applies any heat. After heat is applied and MR data 825 representing an updated image of tissue 860 is obtained, the resulting phase difference between the reference image pixel and the updated image pixel represents the temperature change. In order to determine the absolute temperature of a pixel, the change in temperature between the updated image and the reference image must be added to the reference image absolute temperature, which is known by measurement, empirical data, etc. In one embodiment, MR system 870 is capable of determining the absolute temperature of tissue 860. It will be appreciated that other methods of processing MR data 825 to produce images displayed by GUI 250 and/or to process to control the output of heat generating system 130 may be used without departing from the spirit or the scope of the present invention.

Irreversibly damaged tissue is displayed using damage image 245 (FIG. 2) in GUI 250. A portion of tissue 860 is considered irreversibly damaged when the cells of the tissue portion are dead, or damaged enough, through protein denaturization, water vaporization, etc., that it is determined, using empirical data, previous experience, or models, that the cells will likely die within a relatively short time span. In one embodiment, damage image 245 is constructed using the temperature history for a given portion of tissue 860. One method of determining tissue damage using temperature history is to determine a total amount of heat absorbed by tissue in an area. This may be achieved by keeping a summation of all temperatures measured for a given portion of tissue 860. If the sum total of heat for the given portion exceeds a predetermined value, the cells in that portion are considered dead or dying. In one embodiment, the Arrhenius rate equation may be used to calculate irreversible cell damage as a function of the temperature history. The Arrhenius rate equations is commonly expressed as follows:

$$\Omega = \int A^* e^{-Ea/(RT)} dt$$

Wherein:
 A is the frequency factor constant for a given tissue type;
 Ea is the activation energy value specific to the type of tissue;
 R is the Universal Gas Constant; and
 T is the temperature history of the tissue as a function of time; and
 a cell is considered dead or dying if the value of $\Omega$ is greater than or equal to one when the equation is evaluated.

The Arrhenius rate equation is integrated with respect to time for a given location of tissue 860, and if the integrated value is greater than a determined value, then the cells in the location are considered irreversibly damaged. It will be appreciated that the determined value, based on tissue type, may be a result of empirical analysis, a user's experience, models, or theory. As it is very rare to have a defined, continuous equation for cell temperature as a function of time, the Arrhenius rate equation is usually evaluated numerically by using linear interpolation between temperature history points. It will be appreciated that as the time difference between temperature history points decreases, the degree to which linear interpolation emulates the real temperature history of a given location of tissue 860 increases.

As discussed previously, damage distribution data, in addition to (or in place of) temperature data, may be used to determine the feedback control of laser 805. Since the damage to a cell in many cases is dependent on the properties of the cell type, location, and the like, the appropriate values for constants of the Arrhenius equation must be determined. The user may use previous experience, tables, or may load the values from a database or a file. Alternately, the values could be hardcoded into software used by data processor 120, automatically uploaded from a database, etc. Incorrectly determining the total heat needed may result in charring of the cells if the history of heat received is enough to char the cells or if an absolute maximum temperature is exceeded. Similarly, if not enough heat is absorbed by the cells in tissue 870, or if a minimum temperature needed to cause cell death or irreversible damage is never reached, the cells will not be dead or dying, although they are displayed as dead or dying cells in damage image 245 (FIG. 2).

In the previous detailed description of the embodiments of the present invention, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that logical, mechanical, chemical and electrical changes may be made without departing from the spirit or scope of the invention. To avoid detail not necessary to enable those skilled in the art to practice the invention, the description may omit certain information known to those skilled in the art. The previous detailed description is, therefore, not to be taken in a limiting sense, and the scope of the present invention is defined only by the appended claims.

We claim:

1. A system comprising:
 a data processing module having a plurality of input output nodes; and a memory having a plurality of input output nodes coupled to the plurality of input output nodes of the data processing module, wherein the memory stores operational instructions that cause the processing module to:
  receive input data from a detection device that interrogates a tissue portion with radiation as part of acquiring the input data, wherein the input data corresponds to a tissue portion and includes temperature sensitive information;
  determining at the data processor a property of the tissue portion based on temperature sensitive information, wherein operation of a heat generating device is to be based on the first characteristic; and
  displaying the first property to the operator of the heat generating device, wherein the value of the first property effects the operators control of the heat generating device.

2. A system comprising:
a data processing module having a plurality of input output nodes; and
a memory having a plurality of input output nodes coupled to the plurality of input output nodes of the data processing module, wherein the memory stores operational instructions that cause the processing module to:
  receive input data from a magnetic resonance device which interrogates a portion of an animal body with radiation as part of acquiring the input data, wherein the input data corresponds to a portion of the animal body and includes temperature sensitive information;
  further receive additional input data wherein additional input data is from a user, and wherein the additional input data contains information corresponding to a desired heating result;
  determine a first characteristic for a heat generating device based on the temperature sensitive information, wherein operation of the heat generating device is to be based on the first characteristic; and
  provide control data to the heat generating device, wherein the control data is based on the first characteristic.

3. The system of claim 2, wherein the magnetic resonance device is equipped to acquire proton resonance frequency sensitive images.

4. The system of claim 3, wherein the laser based device delivers laser energy to a target using a fiberoptic applicator.

5. The system of claim 2, wherein the input data represents one or more data sets acquired using a proton resonance frequency sensitive method.

6. The system of claim 2, wherein the step of receiving input data includes receiving the input data at a network interface.

7. The system of claim 2, wherein the additional input data which is further received includes one or more of: a user selected point, line, area, volume, plane, locus, perimeter, temperature, damage, and intensity.

8. The system of claim of claim 2, wherein the additional input data is specified relative to a magnetic resonance based image of a portion of an animal body representing one or more of: a physical structure, a temperature distribution, a tissue damage distribution, a contrast-enhanced image, and a processed contrast-enhanced image.

9. The system of claim 2, wherein the information corresponding to a desired heating result includes specification of one or more limit temperatures.

10. The system of claim 2, wherein the information corresponding to a desired heating result includes specification of one or more points to be damaged.

11. The system of claim 2, wherein the information corresponding to a desired heating result includes specification of one or more points to be spared from damaged.

12. The system of claim 2, wherein the step of determining includes determining the control data using a first characteristic and a rule set.

13. The system of claim 2, wherein the beat generating device is a laser based device.

14. The system of claim 2, wherein the step of providing includes providing command data to the heat generating device.

15. The system of claim 2, wherein the step of determining includes determining the first characteristic based upon the temperature sensitive information of a first portion of the input data, wherein the first portion of the input data corresponds to a first region of the animal body.

16. The system of claim 15, wherein the step of determining includes determining a tissue damage of the first region of the animal body.

17. A method comprising the steps of:
receiving input data at a data processor, wherein the input data is from a detection device that interrogates a tissue portion with radiation as part of acquiring the input data, wherein the input data corresponds to a tissue portion and includes temperature sensitive information;
determining at the data processor a first property of the tissue portion based on temperature sensitive information, wherein operation a heat generating device is to be based on the first property; and
displaying the first property to the operator of the heat generating device wherein the value of the first property effects the operator's control of the beat generating device.

18. The method of claim 17, wherein the step of receiving input data includes the detection device being a magnetic resonance device.

19. The method of claim 18, where in the magnetic resonance device is an imaging system equipped to generate proton resonance frequency sensitive images.

20. The method of claim 17, wherein the operation of the beat generation device results in heating of the tissue portion.

21. The method of claim 17, wherein the first property is tissue temperature.

22. The method of claim 21, wherein the temperatures are used in an Arrhenius rate equation to estimate the amount of tissue that is irreversibly damaged.

23. A method comprising the steps of:
receiving input data at a data processor, wherein the input data is from a magnetic resonance device which interrogates a portion of an animal body with radiation as part of acquiring the input data, wherein the input data corresponds to a portion of the animal body and includes temperature sensitive information;
further receiving additional input data at a data processor, wherein the additional input data is from a user, and wherein the additional input data contains information corresponding to a desired heating result;
determining at the data processor a first characteristic for a heat generating device based on the temperature sensitive information and the desired heating result, wherein operation of the heat generating device is to be based on the first characteristic; and providing control data to the heat generating device, wherein the control data is based on the first characteristic.

24. The method of claim 23, wherein the magnetic resonance device is equipped to acquire proton resonance frequency sensitive images.

25. The method of claim 24, wherein the input data represents one or more data sets acquired using a proton resonance frequency sensitive method.

26. The method of claim 25, wherein the data sets correspond to one or more magnetic resonance images.

27. The method of claim 25, wherein the data sets correspond to complex frequency domain data.

28. The method of claim 25, wherein the temperature sensitive information includes the complex phase of the data contained in the data sets.

29. The method of claim 23, wherein the magnetic resonance device is equipped to acquire T1-weighted images.

30. The method of claim 29, wherein the input data represents one or more data sets acquired using a T1-weighted imaging method.

31. The method of claim 30, wherein the data sets correspond to one or more magnetic resonance images.

32. The method of claim 30, wherein the data sets correspond to complex frequency domain data.

33. The method of claim 30, wherein the temperature sensitive information includes the magnitude of the data contained in the data sets.

34. The method of claim 23, wherein the step of receiving input data includes receiving the input data at a network interface.

35. The method of claim 34, wherein the network interface transmits and/or receives data using a Transmission Control Protocol/Internet Protocol (TCP/IP) protocol.

36. The method of claim 35, wherein network interface transmits and/or receives data using a Server Message Block (SMB) protocol.

37. The method of claim 35, wherein network interface transmits and/or receives data using a File Transfer Protocol (FTP) protocol.

38. The method of claim 37, wherein data processor periodically queries magnetic resonance device for the presence of new input data.

39. The method of claim 38, wherein the step of periodically querying magnetic resonance device consists of periodically requesting the status of a file or file resident on storage connected to or in memory of magnetic resonance device.

40. The method of claim 35, wherein network interface transmits and/or receives data using a Network File Sharing (NFS) protocol.

41. The method of claim 40, wherein input data is periodically transferred to data processor by magnetic resonance device.

42. The method of claim 35, wherein network interface transmits and/or receives data using one or more of
   an Apple Filing Protocol File System (AFPFS) protocol and
   an Apple Talk protocol.

43. The method of claim 23, wherein the additional input data which is further received includes one or more of a user selected point, line, area, volume, plane, locus, perimeter, temperature, damage, and intensity.

44. The method of claim 43, wherein the additional input data is specified relative to a magnetic resonance based image of a portion of an animal body representing one or more of: a physical structure a temperature distribution, a tissue damage distribution, a contrast-enhanced image, and a processed contrast-enhanced image.

45. The method of claim 44, wherein the magnetic resonance based image is constructed from mathematical operations performed on one or a series of such images.

46. The method of claim 45, wherein the one or a series of such images were acquired prior to initiation of heating.

47. The method of claim 45, wherein the one or a series of such images are acquired after administration of a magnetic resonance contrast agent.

48. The method of claim 23, wherein the information corresponding to a desired heating result includes specification of one or more limit temperatures.

49. The method of claim 23, wherein the information corresponding to a desired heating result includes specification of one or more points, areas, loci, and/or perimeters to be damaged.

50. The method of claim 23, wherein the information corresponding to a desired heating result includes specification of one or more points to be spared from damage.

51. The method of claim 23, wherein the information corresponding to a desired heating result includes specification of one or more areas to be spared from damage.

52. The method of claim 23, wherein the information corresponding to a desired heating result includes specification of one or more loci to be spared from damage.

53. The method of claim 23, wherein the information corresponding to a desired heating result includes specification of one or more perimeters to be spared from damage.

54. The method of claim 23, wherein the step of determining includes determining the control data using a first characteristic and a rule set.

55. The method of claim 54, wherein the rule set consists of one or more temperature limits associated with one or a plurality of locations.

56. The method of claim 55, wherein the first characteristic of the heat generating device is to have its output intensity reduced.

57. The method of claim 23, wherein the step of determining includes determining the control data based on the first characteristic and on subsequent user input, wherein subsequent user input is based on the first characteristic.

58. The method of claim 23, wherein the heat generating device is a laser based device.

59. The method of claim 58, wherein the laser based device delivers laser energy to a target using a fiberoptic applicator.

60. The method of claim 59, wherein the fiberoptic applicator includes diffusing tip.

61. The method of claim 58, wherein the laser based device is a diode laser.

62. The method of claim 61, wherein the diode laser device operates at one or a plurality of wavelengths at or around 980 nm.

63. The method of claim 61, wherein the diode laser device operates at one or a plurality of wavelengths at or around 940 nm.

64. The method of claim 61, wherein the diode laser device operates at one or a plurality of wavelengths at or around 810 nm.

65. The method of claim 23, wherein the step of providing includes providing command data to the heat generating device.

66. The method of claim 65, wherein the command dam is communicated to the heat generating device using one or more of: a point-to-point interfere, an IEEE-488 interface, an RS-232 interface, a parallel interface, a serial interface, and digital I/O interface.

67. The method of claim 65, wherein the command data consists of a pulse-width-modulation signal which controls the output intensity of the heat generating source.

68. The method of claim 23, wherein the step of determining includes determining the first characteristic based upon the temperature sensitive information of a first portion of the input data, wherein the first portion of the input data corresponds to a first region of the animal body.

69. The method of claim 68, wherein the step of determining includes determining a tissue damage of the first region of the animal body.

70. The method of claim 69, wherein determining the tissue damage includes evaluating a mathematical function that is dependent upon the temperature sensitive information for a specific location with respect to time to determine a damage indicator.

71. The method of claim 70, wherein the mathematical function is based on an Arrhenius rate process.

72. The method of claim 71, wherein the mathematical function comprises $$\int A e^{\frac{-Ea}{RT(t)}} dt,$$

where A is the frequency factor constant for a tissue, Ea is the activation energy constant for the tissue, R is the universal gas constant, t is time, and T(t) is the time-dependent temperature of the tissue.

73. The method of claim 72, wherein the mathematical function is evaluated numerically.

74. The method of claim 73, wherein interpolation is used to increase the number of points T(t) at which the friction is evaluated.

75. The method of claim 23, wherein the input data consists of one or more data sets acquired using magnetic resonance imaging.

76. The method of claim 75, wherein the data sets represent images along one or more planes through the animal body.

77. The method of claim 75, wherein at least two of the planes are orthogonal.

78. The method of claim 76, wherein at least two of the planes are parallel.

79. The method of claim 75, wherein at least two of the planes are oblique.

80. The method of claim 75, wherein the data sets are used to construct a three-dimensional rendering of portions of the animal body.

81. The method of claim 75, wherein the data sets are used to construct a three-dimensional rendering of damage to tissues in portions of the animal body.

82. The method of claim 75, wherein the data sets are used to construct a three-dimensional rendering of temperature distributions in tissues in portions of the animal body.

* * * * *